United States Patent
Jackson (10) Patent No.: US 10,124,155 B2
(45) Date of Patent: Nov. 13, 2018

(54) TISSUE EXPANDER WITH SEPARABLE COATING

(71) Applicant: OXTEX LIMITED, Oxford (GB)

(72) Inventor: David Edward Jackson, Wallingford (GB)

(73) Assignee: Oxtex Limited, Oxford (GB)

( * ) Notice: Subject to any disclaimer, the term of this patent is extended or adjusted under 35 U.S.C. 154(b) by 193 days.

(21) Appl. No.: 14/912,286

(22) PCT Filed: Aug. 13, 2014

(86) PCT No.: PCT/GB2014/052485
§ 371 (c)(1),
(2) Date: Feb. 16, 2016

(87) PCT Pub. No.: WO2015/022536
PCT Pub. Date: Feb. 19, 2015

(65) Prior Publication Data
US 2016/0199629 A1    Jul. 14, 2016

(30) Foreign Application Priority Data

Aug. 16, 2013 (GB) ..................... 1314707

(51) Int. Cl.
*A61M 29/02* (2006.01)
*A61B 90/00* (2016.01)
*A61B 17/00* (2006.01)

(52) U.S. Cl.
CPC ............. *A61M 29/02* (2013.01); *A61B 90/02* (2016.02); *A61B 2017/00526* (2013.01);
(Continued)

(58) Field of Classification Search
CPC .......... A61M 29/02; A61M 2202/0007; A61B 2017/00792; A61B 2017/00898;
(Continued)

(56) References Cited

U.S. PATENT DOCUMENTS

| 4,157,085 A | 6/1979 | Austad |
| 5,005,591 A * | 4/1991 | Austad ................... A61B 90/02 |
| | | 128/899 |

(Continued)

FOREIGN PATENT DOCUMENTS

| CN | 102639163 A | 8/2012 |
| EP | 2470233 | 7/2012 |

(Continued)

OTHER PUBLICATIONS

Search Report and First Office Action issued by the State Intellectual Property Office of the People's Republic of China in connection with Chinese Application No. 201480056404.0, dated Jul. 3, 2017, 6 pages.

(Continued)

*Primary Examiner* — Katrina Stransky
(74) *Attorney, Agent, or Firm* — Meunier Carlin & Curfman LLC (57) ABSTRACT

The present invention provides a tissue expander (10) comprising a self-inflating core (12 or 2e) having a non-inflated state and an inflated state and a coating (14) surrounding said core (12 or 12e), in which said core (12 or 12e) comprises a compacted self-inflating material and said coating comprises a fluid impermeable material having a plurality of apertures therethrough for allowing the passage of fluid to the core (12 or 12e) and in which the coating (14) is separable or separated from the core (12 or 12e) such as to allow the coating to provide a support function during use. The invention also provides a method of manufacturing the product.

20 Claims, 6 Drawing Sheets

(52) U.S. Cl.
CPC ........... *A61B 2017/00792* (2013.01); *A61B 2017/00898* (2013.01); *A61B 2017/00942* (2013.01)

(58) Field of Classification Search
CPC ........... A61B 2017/00942; A61B 90/02; A61F 2250/0004
See application file for complete search history.

(56) References Cited

U.S. PATENT DOCUMENTS

| | | | |
|---|---|---|---|
| 5,192,326 A | 3/1993 | Bao et al. | |
| 5,496,368 A | 3/1996 | Wiese | |
| 6,520,989 B1 | 2/2003 | Eaton | |
| 2002/0091443 A1 | 7/2002 | Yoon | |
| 2011/0112383 A1 | 5/2011 | Voss et al. | |
| 2012/0265165 A1* | 10/2012 | Bucknall | A61L 27/26 604/500 |
| 2014/0142523 A1* | 5/2014 | Steinbaugh | A61F 13/00008 604/304 |

FOREIGN PATENT DOCUMENTS

| | | |
|---|---|---|
| GB | 2139898 A | 11/1984 |
| WO | 2007080391 A2 | 7/2007 |
| WO | 2011051731 A2 | 5/2011 |

OTHER PUBLICATIONS

International Preliminary Report on Patentability issued by the International Bureau of WIPO from PCT Application No. PCT/GB2014/052485 dated Feb. 16, 2016, 7 pages.

International Search Report and Written Opinion of the International Searching Authority from PCT Application No. PCT/GB2014/052485, dated Oct. 31, 2014, 11 pages.

Search Report of the GB Intellectual Property Office from Application No. GB1314707.9, dated Feb. 12, 2014, 4 pages.

Examination Report of the GB Intellectual Property Office from Application No. GB1314707.9, dated Oct. 5, 2015, 2 pages.

* cited by examiner

TISSUE EXPANDER WITH SEPARABLE COATING

The present invention relates to expandable components and relates particularly but not exclusively to components known as tissue expanders. Such expanders are used by medical, veterinary and dental staff to cause the expansion of patient tissue in advance of corrective or supplemental surgery and generally are such as to have a controlled rate of expansion and may also be configured to have a delayed expansion capability. In one aspect the present invention relates particularly to the inter-relationship between the coating and the expandable material within the coating in which the costing is separable from the expandable material.

Tissue expanders are now a key component in reconstructive plastic surgery and are used in, for example, the treatment of congenital abnormalities and acquired defects.

One known form of tissue expander is described in EP10776126 and from which it will be appreciated that they generally comprise a dried then compressed material which, when re-hydrated will expand to re-gain any height lost during compression. The rate of expansion may be controlled by coating the expandable material in a bio-degradable coating which, upon insertion in the patient, will degrade upon exposure to moisture and then allow the moisture to access the expandable de-hydrated material such as to hydrate it and cause it to expand. An alternative approach is to make the expandable material as an Inter-penetrating Network of bio-degradable material and expandable material which, in combination, provide the delay and the expansion. The expandable material can be formed from a number of materials but new forms of hydrogel (a gel in which water is the dispersion medium) are of particular use in such applications. Such expanders are generally known as "self-inflating tissue expanders".

Whilst the above-mentioned arrangement is able to offer some degree of control over the delay and the rate of expansion, it has been found that still further control is required in order to provide an acceptable product. One possible solution is available in GB1314707 which was unpublished at the priority date of this application which provides a tissue expander comprising a self-inflating core having a non-inflated state and an inflated state and a water impermeable coating surrounding said core, in which the coating includes a plurality of first and/or second apertures through said coating which, in operation, act to control the rate of water ingress and allow for the control of any expansion by altering the size, number and possibly also the position of the holes themselves. The invention described in GB1314707 relates most particularly to the particular properties of the expandable material itself in combination with the provision of the holes through the water impermeable layer.

Whilst the above product provides a certain level of improvement, it has been found that a further improvement can be obtained by controlling the inter-relationship between the coating and the expandable core such as to allow the expandable core a greater degree of freedom during the expansion process than might be possible in the prior art arrangements. Still further advantage may be gained by employing the outer coating as a protective coating which interacts with its surroundings in an improved manner such as to provide a better user experience during the use of the expander itself.

Accordingly, the present invention provides a tissue expander comprising a self-inflating core having a non-inflated state and an inflated state and a coating surrounding said core, in which said coating includes a plurality of first and/or second apertures through said coating and wherein said coating and said core are separable from each other and in that said core includes an outer surface and said coating includes an inner surface and further comprises a non-adhered coating having no physical inter-bond between the inner surface of the coating and the outer surface of the core.

Preferably, said coating comprises a fluid impermeable material.

In one arrangement there is provided an inter-coating between the inner surface of the coating and the outer surface of the core. Said inter-coating may comprise a flexible material. Said inter-layer may comprise a moisture permeable layer. Said inter-layer may comprise a water soluble layer.

In a preferred arrangement, said coating comprises a molded coating molded around the core.

Preferably said coating includes one or more circumferentially extending ring portions of greater thickness ($T^2$) than the thickness (T) of the remaining portions of the coating.

Advantageously, said core includes edges having a radius of curvature R and said coating has radius of curvature r adjacent said radius R and wherein said radius r is less than said radius R thereby forming said ring or rings.

The present invention also provides a tissue expander as claimed in any one of claims 1 to 8 comprising an inner core having a top portion, a bottom portion, and a side portion and an outer coating and wherein said coating comprises a coating surrounding said inner core and in physical contact with at least a portion of the side of the core when said inner core is in said non-inflated state and out of contact with said side of the core when said core is in a partially inflated state.

In one arrangement said inner core comprises a multiplicity of separate expandable elements.

Preferably, said separate expandable elements comprise granulated self-expanding material.

Preferably, said inner core comprises a water permeable hydrophilic material.

In one arrangement said one or more of said separate expandable elements include a coating and wherein said coating comprises a water soluble coating.

In one particular arrangement there are provided first and second groups of expandable elements and including different thicknesses of coating on each group of said separate expandable elements.

In one arrangement said coating comprises an envelope having an internal volume and wherein said inner core comprises a plurality of separate expandable elements having a total de-hydrated volume when inserted into said envelope and wherein volume is less than volume.

Preferably, the hydrated volume of said plurality of separate expandable elements is substantially equal to or greater than the internal volume of the envelope.

In one arrangement the tissue expander may comprise a non-expandable base portion forming or integral with a portion of the coating.

The invention also provides a tissue expander as claimed in any one of claims 1 to 19 when in a non-expanded state. In an alternative arrangement the invention provides a tissue expander as claimed in claim in any one of claims 1 to 19 when in a partially expanded state. In a still further arrangement the invention provides a tissue expander as claimed in any one of claims 1 to 19 when in a fully expanded state.

Preferably, the tissue expander includes a semi-permeable barrier material within one or more of said first apertures. Such will help with controlling the rate of water ingress.

Advantageously, the tissue expander includes a semi-permeable barrier material within one or more of said second apertures. Such will further assist with controlling the rate of water ingress.

In one arrangement the said core may include edges and said coating may have has a greater thickness (T) adjacent said edges than at other portions.

In a preferred arrangement said core includes first edges having a radius of curvature R and wherein said coating has second edges adjacent said first edges and having a radius of curvature r less than said first radius of curvature R.

Any of the above may have a core which comprises a hydrophilic self-inflating polymer.

The present invention also provides a method of manufacturing a tissue expander comprising the steps of:
a. selecting a self-inflating hydrophilic core material;
b. forming said selected material to a given height and width;
c. compacting said core material by reducing the height thereof whilst increasing the width thereof such as to produce a compacted core
d. coating said core with a separable resilient fluid impermeable coating; and
e. providing a plurality of first and/or second apertures through said coating.

The above method may include the additional steps of:
f. partially hydrating said self-inflating hydrophilic core material between steps (a) and (b); and
g. de-hydrating said hydrophilic core material between steps (b) and (c).

Advantageously, the method includes the step of forming the core material with edges having a radius of curvature R and coating said coating onto the core by molding said coating around the core.

The method may also provide an advantageous step of forming the coating with edges adjacent the edges of the core and having a radius of curvature r which is less than the radii of curvature R of the edges of the core.

The method may include the further step of providing a semi-permeable material within one or more of said one or more first and/or second apertures.

In an alternative arrangement there is provided a method of manufacturing a tissue expander comprising the steps of:
a. selecting a self-inflating hydrophilic core material;
b. forming said selected material into a plurality of separate expandable elements;
c. providing an envelope having an internal volume;
d. providing a plurality of first and/or second apertures through said envelope; and
e. Inserting a plurality of said expandable elements into said envelope and partially filling said envelope therewith.

This alternative method may also including the additional steps of:
f. partially hydrating said self-inflating hydrophilic core material between steps (a) and (b); and
g. de-hydrating said hydrophilic core material between steps (b) and (c).

This alternative method may also include the step of inserting a semi-permeable material into said one or more apertures and may also include the step of compacting said plurality of expandable elements (12e) between steps (b) and (c).

The present invention will now be more particularly described by way of example only with reference to the accompanying drawings, in which.

By way of background, the present invention employs a self-inflating material such as a polymer gel. The material may employ a hydrophilic polymer network which is capable of absorbing water without dissolution. The hydrophilic properties may be provided by functional groups on the polymer(s) (e.g. hydroxyl, carboxyl or amide functional groups). Preferably the self-inflating polymer network comprises at least one monomer containing —COOH, >C=0, —OH, or —NH$^2$ groups. The resistance to dissolution is a result of the presence of structural cross-linkages, crystalline regions or entanglements. Such materials are typically termed "hydrogels". The hydrogel contains two components, namely the polymer network (i.e. the gel), which is constant in quantity, and a variable aqueous component. In the anhydrous state (prior to implantation), the material is normally referred to as a xerogel. The anhydrous material is hygroscopic and absorbs/adsorbs water from its local environment to hydrate the network. The self-inflating polymer network may swell to many times its dry mass. Typically, the aqueous phase comprises 90% or more, preferably 95% or more of the total mass of the self-inflating polymer network at equilibrium. The expansion of the self-inflating polymer network is driven by the diffusion of water molecules into the polymer network which is due to osmosis and the interaction between the polymer and water molecules in order to reduce the Gibbs free energy of the system when the polymer is introduced into an aqueous environment, i.e. from tissue fluid in vivo. The self-inflating polymer network approaches its equilibrium state when the driving force for the mixing between the polymer species and the solvent is balanced by the restoring force of the chains in the network due to the elasticity of polymer network. Whilst there are number of self-inflating polymers that could be used hydrogels are the most suited to medical applications. It is preferable that the hydrogel comprises functional groups on the polymer (e.g. hydroxyl, carboxyl or amide functional groups or others which provide the hydrophilic properties thereof. The expansion of the above self-inflating polymer is driven by the diffusion of water molecules into the polymer network which is due to osmosis and the interaction between the polymer and water molecules in order to reduce the Gibbs free energy of the system when the polymer is introduced into an aqueous environment, such as may be experienced when inserted within a human or animal body. The self-inflating polymer network approaches its equilibrium state when the driving forces for the mixing between any polymer species and any solvent is balanced by the restoring force of the chains in the network due to the elasticity of the polymer network itself.

It will be appreciated that other forms of self-inflating materials may be used but that materials which adsorb water to create the expansion are particularly useful.

Figure 1:
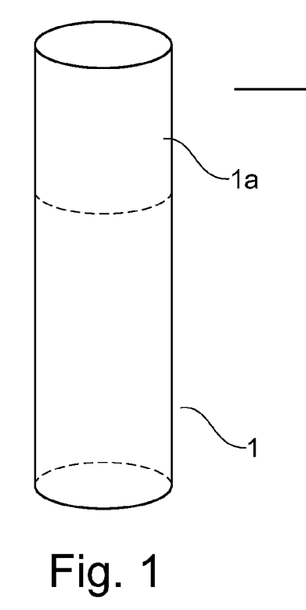
FIG. 1 is a diagrammatic representation of a rod of preformed expandable material.
Figure 2:
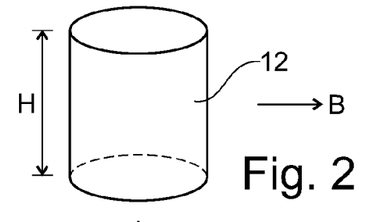
FIG. 2 is a view of a short length of the material shown in FIG. 1 prior to a drying step.
Figure 3:
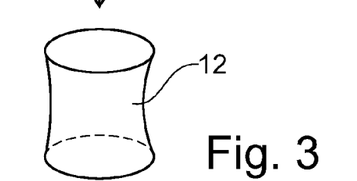
FIG. 3 is a view of the material of FIG. 2 after a drying or de-hydration step has been performed thereon.

A first manufacturing process which may be employed in the manufacture of the present product is illustrated in FIGS. 1 to 3, in which a partially hydrated self-inflating polymer gel is formed into a pre-determined shape 1, a portion of which 1a is cut therefrom to form the shorter portion 12 or core shown first in FIG. 2. The Height H of the core 12 of FIG. 2 is selected to be sufficient to provide the height $H^4$ required in a finished expander after expansion has taken place. It will, therefore, be appreciated that height H may be varied to suit different requirements. The self-inflating polymer is hydrophilic and, therefore, able to absorb water without dissolution and it is this property that is employed to advantage in the present invention.

Figure 6:
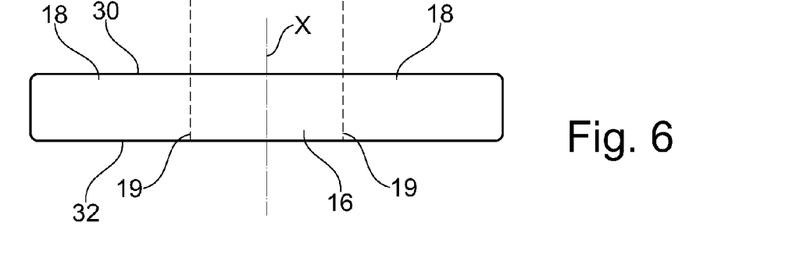
FIG. 6 is a cross-sectional view of the compacted core of the present invention and illustrates the position of a barrier between a central portion and a peripheral portion thereof.
Figure 7:
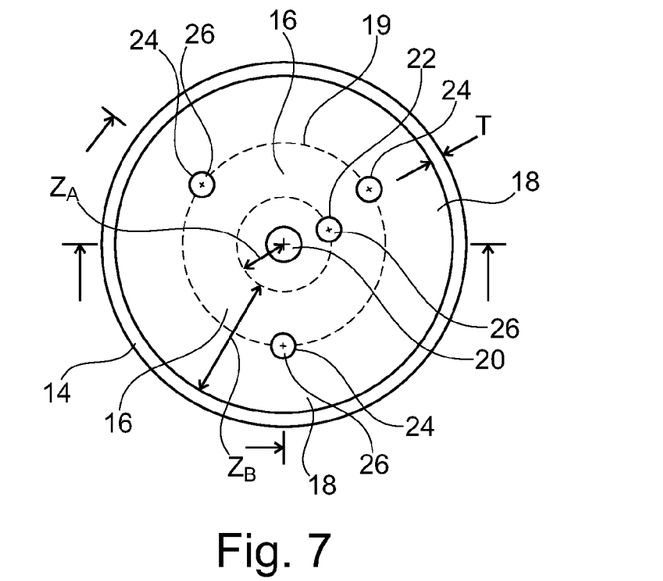
FIG. 7 is a plan view of a the core of FIG. 6 when coated with a coating and provided with apertures therethrough.
Figure 8:
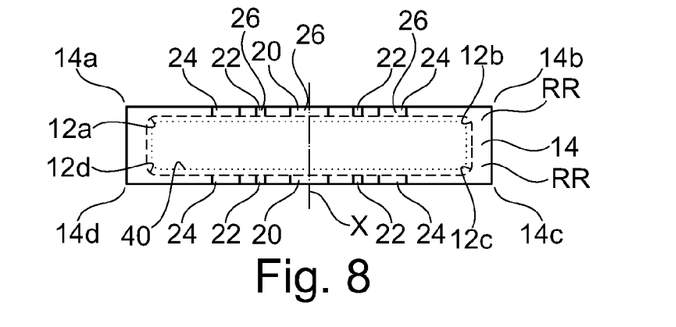
FIG. 8 is a cross-sectional view of the arrangement o FIG. 7.

The core 12 of FIG. 2 is then dried such as to remove the pre-hydration moisture therefrom and produce the component of FIG. 3 which is in the state required for compression forming into the shaped core 12 shown more specifically in FIGS. 6 to 8. It will be appreciated that the partial pre-hydration step will make it easier to cut into a desired shape but that this step may be eliminated if the machinery is available to simply cut the de-hydrated starting material 1 to the desired length. This would also allow for the elimination of the de-hydration step between FIGS. 2 and 3.

Figure 4:
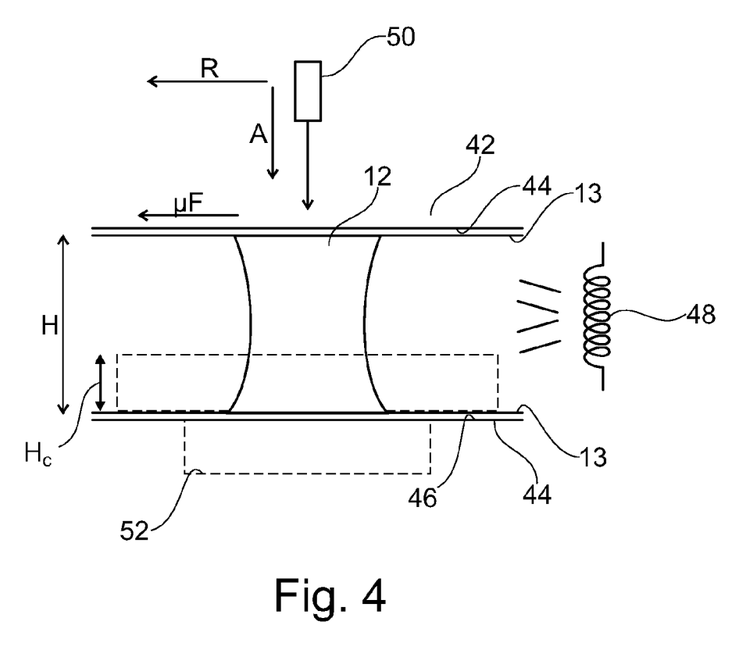
FIG. 4 is a diagrammatic representation of a compaction apparatus and illustrates the shape of the material of FIG. 3 both before and after compaction.

Compression of the core 12 is illustrated diagrammatically in FIG. 4 and from which it will be appreciated that the dried un-compacted core 12 is placed between two compression members 40, 42 having confronting surfaces 44, 46 which, in operation, are preferably shielded from direct contact the core 12 by means of an interlayer 13 in the form of, for example, a layer of silicone or other such suitable inert material. A heater and compression ram, shown schematically at 48, 50 respectively are used to heat and compress the core as detailed below. Compression is done by applying heat and pressure to the core (typically applied in one direction or plane so as to reduce the height H) to provide a subsequent apparent anisotropic expansion principally in the direction of compression. The combination of heat at around or above the glass transition temperature (T[g]) of the polymer and pressure causes the molecular chains to realign. Clearly heating should be lower than the degradation temperature of the polymer. The core 12 may be formed between flat surfaces in which case compaction creates a generally circular lozenge shaped component or it may be formed into a mould shown in dotted format at 52 in FIG. 4.

The compression step reduces the height H of the core whilst increasing the width W, as shown in FIG. 4. The loss in height H corresponds to the increase in height H when the core is re-hydrated back to the hydration level associated with the part-hydrated shape of FIG. 2, hence, the starting height H of the pre-compressed core 12 and the compressed height $H^C$ may be adjusted as required in order to ensure a desired expansion is achieved. During subsequent expansion, the width W will decrease whilst the height H will increase. The compression step itself places the core 12 under a number of forces which include both axial and radial forces shown schematically by arrows A and R. The axial force A is that which is applied to reduce the height H and is directly related to the degree of compression but the radial force R has a component which depends on the frictional properties at the junction of the core material and the confronting surfaces 44, 46. In essence, the greater the degree of friction (μF) the greater the element of radial force R required to compress the core 12.

Figure 5:
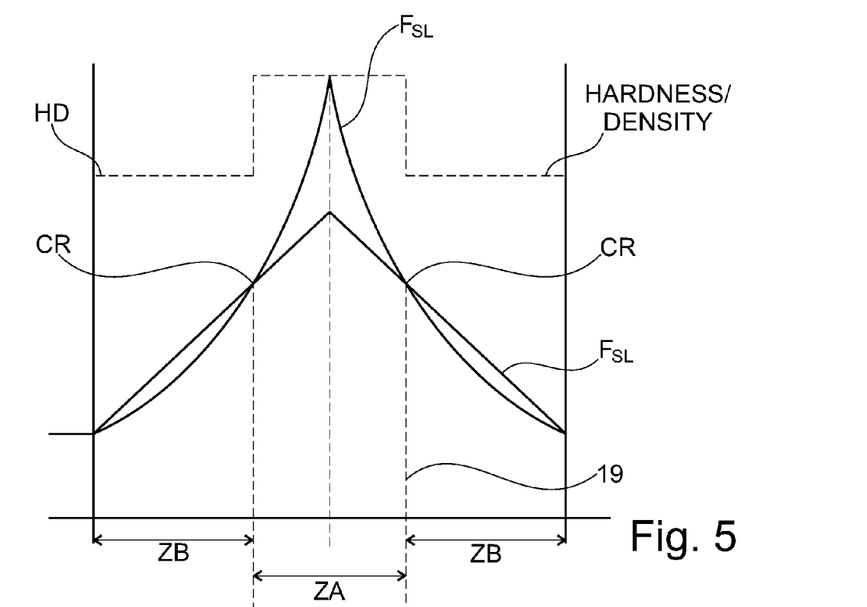
FIG. 5 is a graph illustrating the properties of the compacted core produced by the compaction process associated with FIG. 4.

It has been found that the above-discussed compression process imparts particular properties into the compacted core 12. These properties may be exploited and are described in detail with reference to FIGS. 5 and 6. FIG. 5 is a graph illustrating two properties of the core 12 at various radial positions across the core that are induced and which may be modified by altering the axial compression load and the degree of friction μ at the interface discussed above. The graph of FIG. 5 illustrates the variation across the core in sticking friction $F_{ST}$ and slipping friction $F_{SL}$ where the magnitude of the sticking friction $F_{ST}$ is dependent upon the axial load applied in the direction of arrow F and the slipping friction $F_{SL}$ is related to the coefficient of friction μ at the interface. The sticking friction $F_{ST}$ varies linearly from a maximum at the centre of the core 12 to a minimum at the outer periphery 12a thereof. The slipping friction $F_{SL}$ varies in a non-linear manner from a maximum at the centre of the core 12 to a minimum at the outer periphery 12a thereof.

The force required to overcome the slipping friction is determined form the following formula:

$$F=2k\exp(2\mu/h\,(b/2-x))$$

The force required to overcome the sticking friction is determined by the following formula:

$$F = 2k\left(1 + \left(\frac{\frac{b}{2}-x}{h}\right)\right)$$

Where: F=force, μ=friction, k=shear yield stress, h=height, b/2=radius and x=distance from centre.

As shown in FIG. 5, there is a point of cross-over CR of the magnitude of the frictions and it is this cross-over point which defines a border 19 between what are described herein as a central portion 16 and a peripheral portion 18 if the core 12 itself. The inter-relationship between the magnitudes of slipping friction and sticking friction results in the central portion 16 having a higher (average) hardness and density than the outer peripheral portion 18 and the defining of the border 19 which, it has been found is the point of initiation of any subsequent expansion after hydration. This understanding may be exploited in combination with the present invention such as to create a self-inflating tissue expander 10 in which a controllable delay in expansion may be designed into the finished article and which may be tailored such as to set both the degree of delay and the rate of expansion after insertion into the hydrating medium.

It will be appreciated that the above describes a much preferred arrangement of core 12 but that other forms or expandable cores may be used in association with the coating/core interrelationship defined below.

Figure 9:
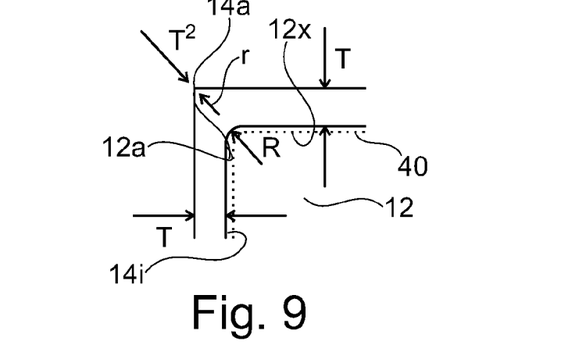
FIG. 9 is a detailed cross-sectional view of a corner portion of FIG. 8 and illustrates the difference between the radii R of the corner of the core and the radii r of the corner of the coating.

Reference is now made to FIGS. 7 to 9 which illustrate a finished product in more detail and from which it will be appreciated that an outer coating 14 having a thickness T which is applied to the core of FIG. 6 in order to provide a barrier to water impregnation. Such a layer may comprise Silicone as this will expand with the core 12 but other materials such as polyurethane or rubber may also be used. In essence, the coating 14 must resist the passage of water therethrough but be sufficiently flexible and/or stretchable as to accommodate the subsequent change in shape and dimension of the core as it expands. Preferably the coating comprises a water impermeable material. A plurality of apertures 20, 22, 24 may be provided in the coating 14 such as to extend through the coating 14 and to one or other or both of the upper and lower surfaces 30, 32 of the core 14 itself. These apertures 20, 22, 24 provide a route through which water can reach the core 12 and may be plugged with a semi-permeable barrier material 26 so as to control the rate of water ingress. The properties of the semi-permeable barrier material 26 may be varied between finished articles such as to provide a more tailored product where the rate of fluid absorption can be pre-defined or they may be set as a constant between finished products if so desired.

The expansion of the core 12 of FIG. 6 initiates at the barrier 19 and, thus, one can vary the delay between insertion and expansion by varying the distance $Z_A$, $Z_B$ of any apertures 20, 24 from the barrier 19. In operation, water will take some time to penetrate through the apertures and then track towards the barrier 19 and, hence, the greater the distances $Z_A$, $Z_B$ the greater the delay in expansion. Clearly, apertures can be placed in association with the central region and/or the peripheral region and may even be placed immediately above the barrier 19 as shown by apertures 22 if it is desired to have zero delay in expansion. The size, position and/or number of the holes 20, 22, 24 may be altered so as to increase or decrease the rate of expansion once it has been initiated.

From the above, it will be appreciated that one is able to take control over the delay before expansion and the rate of expansion once initiated by varying the position, number and size of the holes and the permeability of the holes by the provision of plugs of defined permeability or the elimination thereof as desired. Further, the surgeon may be able to modify the final produce before insertion by simply filling in holes or removing already inserted plugs such as to alter the rate of expansion. Still further, the surgeon may be able to increase the number of holes and/or the position of added holes should that be desired. It will also be appreciated that the coating 14 is in intimate contact with the core 12 which ensures that any fluid which is passed through to the core is channeled in a controlled manner to the barrier region 19 such as to ensure consistency in the delay before expansion takes place.

FIG. 7 provides a cross-sectional view of the tissue expander 10 of FIG. 7 and illustrates a plurality of holes in fluid communication with both the upper and lower surfaces 30, 32 of the core itself. The provision of holes on both sides, whilst not being essential, will help ensure the expansion takes place evenly on both sides and may also ensure a more rapid and complete expansion. The holes may be evenly or unevenly spaced and may be positioned in circumferentially spaced manner around a central axis X if the core. In certain arrangements a central hole may be provided on the axis X which may be used individually or in combination with other holes.

FIG. 8 illustrates some preferred but optional detail associated with the corners of the expander 10 and from which it will be appreciated that the compression of the core 12 will create a lozenge shaped component having corners 14a, 14b, 14c, 14d with a radius of curvature R. It has been found that the coating 14 when applied by dip coasting techniques can be thinner at the corners than might be desirable and premature rupturing of the coating 14 can occur at these positions. In order to solve this problem, the coating may be applied such as to have a thicker coating thickness T at the corners. Such an arrangement can be achieved by injection moulding the coating in a mould containing the compressed core 12 in which the mould has a defined shape with corners adjacent the corners 12a-12d of the core, each of which are of a lesser radius r than radius R. The mould radius r will then translate into a coating radius r at the corners 14a-14d which is less than the radius R, thus creating an increased local thickness T at the corners. This extra thickness at the crucial corner positions will ensure that premature rupturing during expansion is substantially eliminated. A similar issue may arise in connection with core material 12 which is compressed within the mould arrangement shown schematically at 52 in FIG. 4. An alternative solution may present itself in the modification of the corners of the implant 12 such that the radii R associated therewith are sufficiently large as to allow for the deposition of a coating thickness sufficient to survive any expansion of the core without rupturing. An optional method coating may comprise dip coating so long as the thickness of the coating at the corners 12a-12d is sufficient as to retain the integrity of the coating during any subsequent expansion step. If dipping is used, the corners may be rounded with a greater radius of curvature R than might be needed in the moulded arrangement discussed in reference to FIGS. 8 and 9.

The inter-relationship between the expandable core 12 and the coating 14 will now be discussed with reference to FIGS. 10 to 13, from which it will be appreciated that the coating 14 is provided around the core 12 and has an inner surface 14i which will be in contact with the outer surface 12x of the core. Whilst some coatings 14 may be arranged such as to bond to the surface, it has been found that arranging the coating such that it is separable or separated from the core 12 such that it is not tied to the movement of the core 12 improves the patient experience during the expansion steps. In particular, the coating is free to maintain some, if not all, of its pre-insertion shape such that it provided a "space-filling effect" to at least partially fill any void that might be created under the skin as the expander expands. In addition, the fact that the casing retains some of its original width as the expander expands means that the coating acts as a stabilising extension which, in operation, will help keep the expander in the desired orientation and allow for better or more controlled skin expansion.

The coating 14 may be separable by means of having a non-adhered contact with the core 12 or may be physically separated from the core by means of an inter-coating 40 shown as a dotted line in the drawings. Such an inter-coating 40 may comprise a soluble coating applied during the manufacturing process, such as, for example, food starch or PLGA or poly(lactic-co-glycolic acid) or such similar product. Alternatively, the inter-coating 40 may comprise a perforated but flexible material which does not adhere or bond to the coating 14 but which is able to expand with the core 12 and also allow fluid (water or moisture to permeate therethrough such as to reach the core 12. The inter-coating 40 may be made of a water permeable material or from a water impermeable material which is provided with fluid channels (not shown) therethrough.

Figure 10:
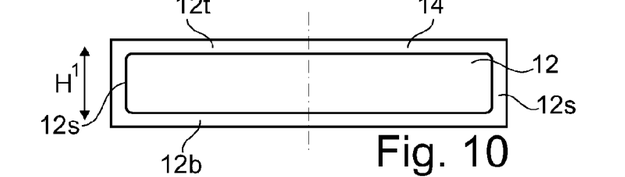
FIGS. 10 to 13 illustrate the different phases of the final product as it changes form the just compacted shape of FIG. 10 to the fully expanded shape of FIG. 13 and further illustrates the interaction the product has with the skin under which it is inserted.

Referring now more particularly to FIGS. 10 to 13, a tissue expander 10 having an expandable core 12 and an outer coating 14 as described above has a low profile with a width W greater than its height $H^1$. FIG. 10 shows the expander 10 prior to being implanting under the skin S of a patient, a portion of which is shown at 52 in FIGS. 11 to 13. It will be appreciated that the skin S will be stretched over the expander and a small void 54 may be formed around the implant 10 as the skin S stretches to a naturally curved contour C. Whilst the void is small the patient may experience little, if any, discomfort but as the void size increases the degree of possible movement of the implant within the void would normally increase, which might be problematic and/or cause some discomfort to the patient. Excessive movement of the implant 10 could cause the implant to topple which would result in the expansion taking place in the wrong direction and may cause undesirable trauma to the patient.

Figure 11:
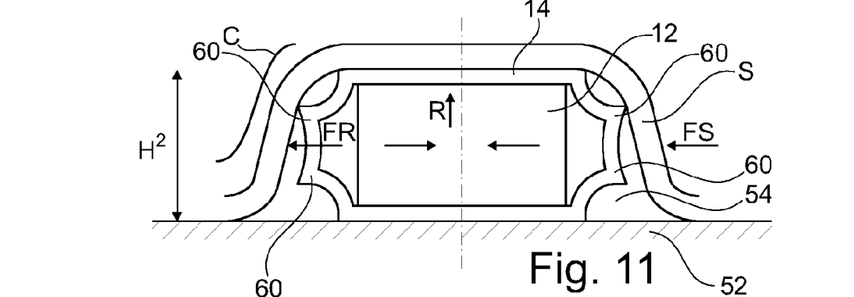

The arrangement of the present invention reduces and possibly eliminates the above-mentioned problems by providing a coating 14 which is separable or separated from the core 12 such that it is able to act within the growing void in a beneficial manner, described in detail below and with particular reference to FIGS. 11 to 13. FIG. 11 shows a partially expanded expander 10 which has risen or expanded in the direction of arrows R whilst shrinking in the direction of arrows I. The coating itself is sufficiently self-supporting as to allow it to separate or remain separated from the core 12 and, in effect, remain at least partially within the void 54 such as to allow it to interact with the surrounding skin 50 in a stabilising manner. If the coating is provided as a relatively thick layer of resilient material such as Silicone or rubber or flexible polyurethane etc. it will have a degree of resilience to squashing or deformation which will provide a resistive force $F^R$ which reacts against and resists any force $F^s$ exerted by the skin S due to the natural resilience of the skin itself. This resilience and the fact that the coating 14 is left within the void 54 will mean that the coating helps space-fill at least a portion of the void and provide a less severe contour C to the skin profile. Preferably, the coating is non water-soluble.

Reducing the contour C and also resisting the deformation of the skin into the void 54 will enhance the patient experience whilst also helping maintain the correct alignment of the expander such as to ensure correct axial stretching of the skin along axis X. This advantage may be further enhanced by creating thicker portions T at the edges 14a, 14b, 14c and 14d which, in operation, help define and maintain an edge to the coating which has good structural integrity in its own right and which forms one or more resilient rings 60 surrounding the core 12. These rings 60 provide much of the structure associated with the resistance force $F^R$ and one may vary the thickness and material as desired such as to create the desired amount of resistance or skin support. It will be appreciated that in this partially expanded state the implant 10 forms a useful product in its own right and it may be used in this state as an initial implant in some patients, particularly in regions where there is already excess skin or where a void already exists such as through trauma to the body. Such use will have a semi-restorative effect in as much as the implant and the separate coating will at least partially space fill the existing void or take-up any slack thee may be in the skin. For this reason, this form of the implant may also be a commercial product and is, therefore, claimed herein.

Figure 12:
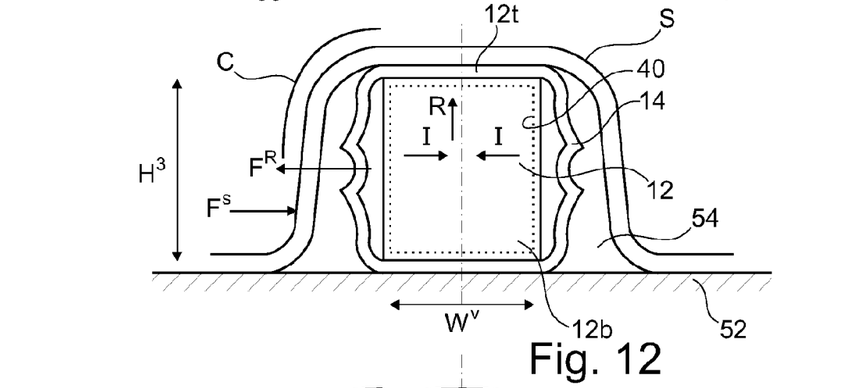

Further expansion of the expander through the adsorption of water or fluid from the patient's body and through the coating 14 results in the sides of the core 12 shrinking in further and the height of the core H increasing from H2 in FIG. 11 to H3 in FIG. 12. At this stage (FIG. 12) the core 12 is partially expanded and close to having re-established the pre-dried shape and size shown in FIG. 2 and will have caused significant stretching of the skin S in the desired direction of along axis X. It will be appreciated that the skin itself will also have closed in around the implant 10 such as to reduce the width $W^V$ of any void 54 and that the sides of the coating 14 will also have shrunk inwardly in a similar manner due to the pulling effect exerted by the expansion along axis X. The rings 60 and the sides of the coating will still be slightly spaced from the core 12 and will still act to at least partially space-fill any void 54 that might exist.

Figure 13:
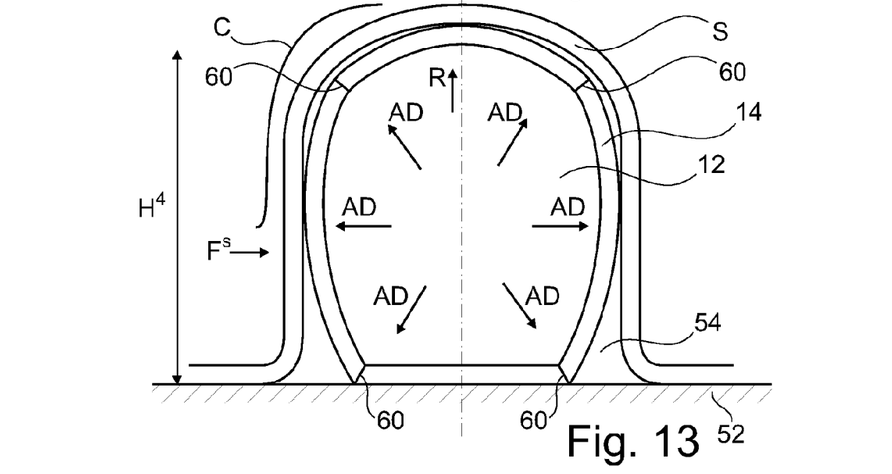

Still further expansion of the implant from that shown in FIG. 12 to the fully expanded state shown diagrammatically in FIG. 13 will take place over a period of time determined by the rate of diffusion of water into the core 12 and will be as a result of the core 12 expanding approximately equally in all directions as indicated by arrows AD. The fully expanded size (both height $H^4$ and width) will exceed that of the partially hydrated size associated with the cut section of FIG. 2. In the final or fully expanded shape, the coating 14 is likely to be in close contact with the core 12 once again and is also likely to be under tension as the expansion will now be beyond the volume of the pre-implanted implant of FIG. 10. The fact that the coating is flexible, resilient and stretchable allows it to stretch and conform to the desired final shape which is, to some extent, at least partially dependent upon the tension provided by the skin S and the shape of any void into which the implant may have been placed. For this reason, the reader will appreciate that the arrangement of FIG. 13 is purely diagrammatic. The reader will also appreciate that the rings 60 will provide some degree of retaining force and this force may be used to constrain the shape of the final product.

The present invention also provides a method of manufacturing a tissue expander 10 as described above including the steps of first selecting a hydrated self-inflating hydrophilic core material and then forming said selected material to a given height H and width W by, for example, cutting from a partially hydrated length thereof. The cut length is then dried to remove as much moisture as possible which will cause the material to shrink in height H and width W which is required prior to the next step which is compaction. Alternatively, the length may be cut from a de-hydrated source and the re-hydration step eliminated. The core 12 is then compacted between, for example, the compression members 42, 44 of FIG. 4 such as to reduce the height H thereof whilst increasing the width W such as to produce a compacted core 12 in the shape of a lozenge which, by virtue of the compaction process will have an inner region of a first, higher, (average) hardness/density HD and a peripheral region 18 of a second, lower, (average) hardness/density hd, a border 19 between said central region 16 and said peripheral region 18.

The compaction process itself is controllable in as much as the rate of compaction, the temperature and the degree of friction can be controlled. Compression rates will depend on the materials being used and the glass transition temperature thereof as well as the degree of heating undertaken during pressing. The degree of friction between the compressing core 12 and the compression members 42, 44 is also important and can be controlled by the application of the interlayer of silicone sheet 13. The sliding properties of the sheet helps reduce the slipping friction µF which is present when the core is squashed radially outwardly and alteration of the friction will affect the profile of the slope shown in FIG. 5. It will, therefore, be appreciated that one may alter the point at which the slipping friction and sticking friction profiles of FIG. 5 cross each other and, as this crossing point defines the barrier 19, it is possible to define the position of the barrier 19 in any formed core This is important as being able to define the position of the barrier 19 allows one to alter the position of the expansion initiation point as such takes place from the barrier portion 19 itself. Also, being able to control the position of the barrier portion 19 and ensure it is at a set position will allow one to accurately position any apertures 20, 22, 24 relative thereto such as to accurately set the delay before expansion takes place.

The next step comprises coating the core 12 with a protective coating designed to control ingress of water into the core 12. Whilst a number of coatings 14 can be used, it has been found that a Silicone 13 layer lends itself to the present application as it has a good degree of flexibility, accommodates the desired expansion of the core 12 and is able to accommodate the formation of apertures 20, 22 as and where desired. Whilst the coating 14 may be applied by dip coating, the present applicants have realised that dip coating often results in a thinning of the coating at the edges 12a-12d of the core which can be undesirable as the coating can rupture during expansion which will result in water penetration in an uncontrolled manner and more rapid and uncontrolled expansion of the core 12 than may be desired. In order to overcome this problem, the present invention may include the step of forming the core material 12 with edges having a radius of curvature R and coating said coating 14 onto the core 12 by moulding said coating 14 around the core 12 and the step of forming the coating material 14 with edges 14e adjacent the edges 12e of the core and having a radii of curvature r which is less than the radii of curvature R of the edges of the core 12. A plurality of apertures 20, 22, 24 as discussed above are then provided through said coating 14. The coating 14 is preferably provided in the form of a water impermeable coating and the apertures 20, 22, 24 may be formed during the coating process.

Figure 14:
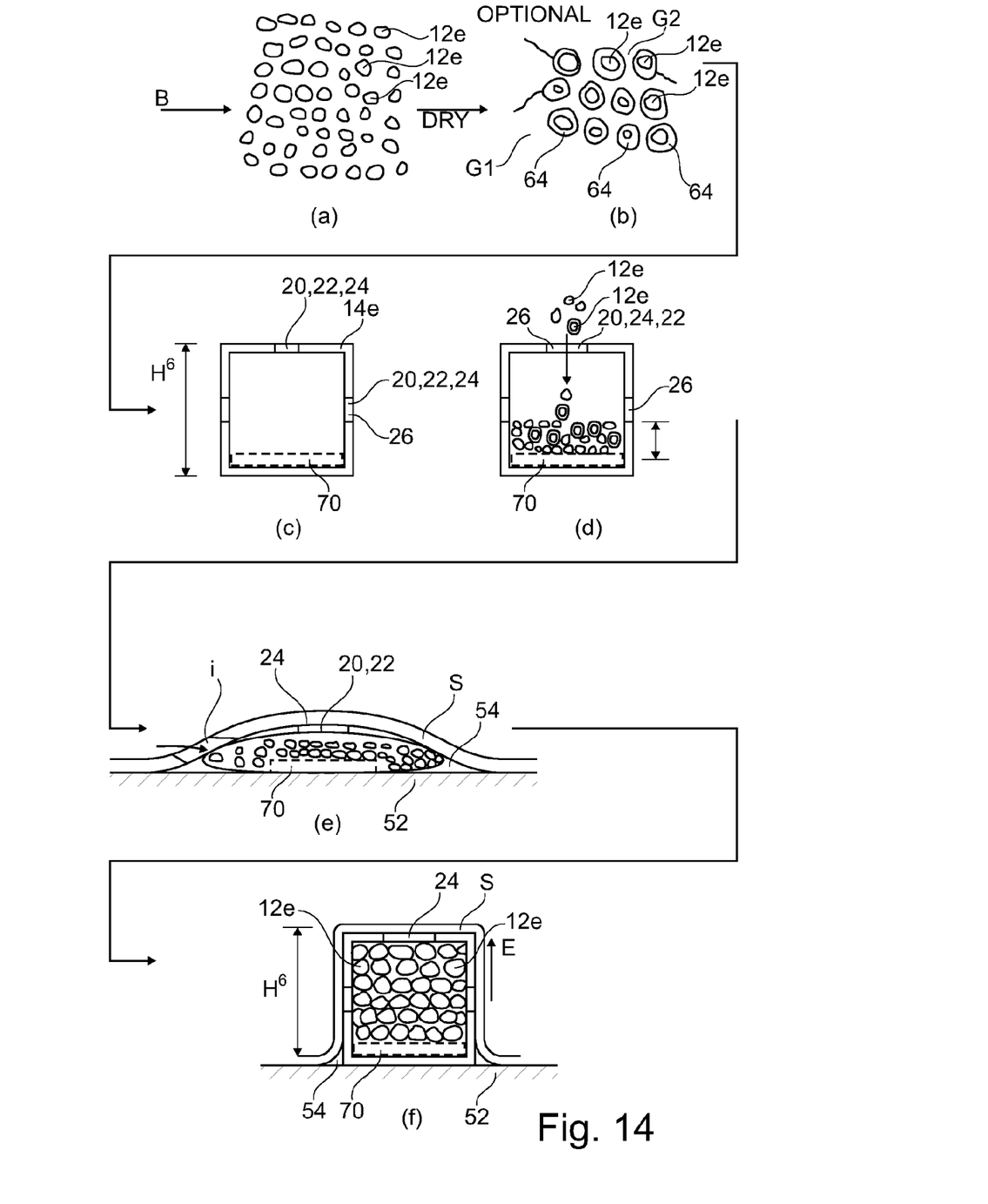
FIGS. 14 and 15 illustrate some optional variations in the shape of the finished article.

An alternative form of expander and manufacturing method is disclosed with reference to FIG. 14 which creates a multiplicity or plurality of separate expandable elements 12e by, for example, cutting, grinding or simply mincing the material described with reference to FIG. 2. The material may be processed in a semi-hydrated state or a fully dehydrated state depending upon the power and type of machine available for the process. If the formation is done in a semi-hydrated state then the elements 12e are then dried to remove as much water therefrom as possible before proceeding to the next stage of the process. An optional step may include the compaction of the dried elements 12e. The final form of the elements 12e may be of a granular nature. The next stage may include the optional step of applying a water-soluble coating 64 to one or more of the separate elements 12e. The thickness of the coating on first and second groups G1, G2 of expandable elements 12e may have different thicknesses such as to allow for the progressive penetration of water into the elements themselves 12e. Such may be used to advantage when it is desirable to control the rate of expansion as some elements 12e will be exposed to the water later than others. In this alternative form of tissue expander 10, the coating comprises an envelope 14e having an internal volume $V^1$ which is selected to be as required in the final fully expanded state of the expander 10. The final shape of the expander may also be defined in advance by selecting the height $H^6$ to correspond with that desired. The remaining dimensions may also be pre-defined in the formation of the envelope and are, preferably, selected such as to provide the final fully expanded expander 10 with the overall shape and dimensions desired. Such an envelope 14e may be formed by simple injection moulding around a dissolvable core (not shown) or by film coating onto the outside of a removable or dissolvable core (not shown). The envelope 14e is formed with one or more apertures 20, 22, 24 through which a plurality of said separate elements 12e are inserted such as to partially space fill the interior of the envelope before being sealed therein by the insertion of a water impermeable plug 26 into said one or more apertures 20, 22, 24. Preferably, the volume $V^2$ of the elements 12e inserted is selected to be such as to allow for them to initially occupy a volume less than $V^1$ but completely space fill the volume $V^1$ once fully hydrated. It will, however, be appreciated that the alternative options of partial filling of volume $V^1$ or over-filling of volume $V^1$ upon full hydration is also possible. These options will, however, come with some disadvantages of slightly reduced dimensional stability and/or increased pressure being exerted on the envelope 14e. As shown in FIGS. 14(C) to 14(f), there may be provided an optional non-expandable base portion 70 formed into the envelope 14e during the manufacturing process. Such a base portion 70 will provide a base against which the expansion can react and further provide a structure with dimensional stability which will help the insertion process as it will help define and retain the shape of the implant 10 during the insertion step. The base 70 will further assist by increasing the dimensional stability of the bottom portion of the implant 10 which is the portion placed against the hard surface 52 under the patient's skin S. FIG. 14(e) illustrates the implant of FIG. 14(d) after it has been inserted through a small incision i through the skin S if a patient and from which it will be appreciated that the fact that the envelope 14e is only partially space filled with elements 12e means it may be deformed or squashed to aid easy insertion. The elements 12e will re-distribute themselves as necessary to accommodate the space within the void 54 and adopt a relatively low profile under the skin S which is in contrast with the arrangement of FIG. 10 which, being more rigid, has less freedom to do so. This lower profile will create less initial skin stretching and will, therefore, induce less irritation. Expansion of the implant 10 of FIG. 14(e) through water ingress through the semi-permeable material 26 will result in the implant adopting the shape of FIG. 14(f) in which the height $H^6$ is equal to that of the starting size of the envelope 14e. As, in the preferred arrangement, the total fully hydrated volume $V^2$ of the elements 12e is selected to be equal to the total initial volume $V^1$ of the envelope, the elements 12e will not place the envelope 14e under strain but will place the skin under strain as they expand.

Figure 15:
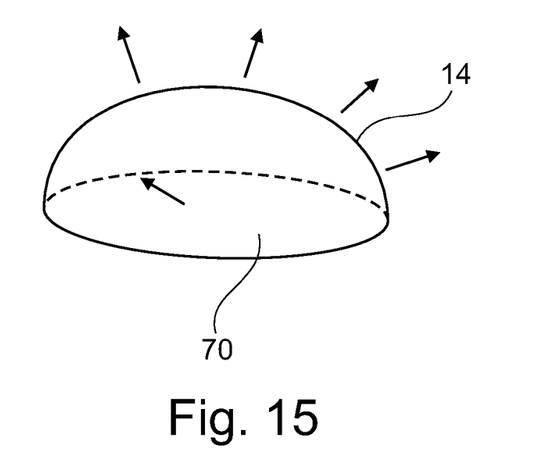
Figure 16:
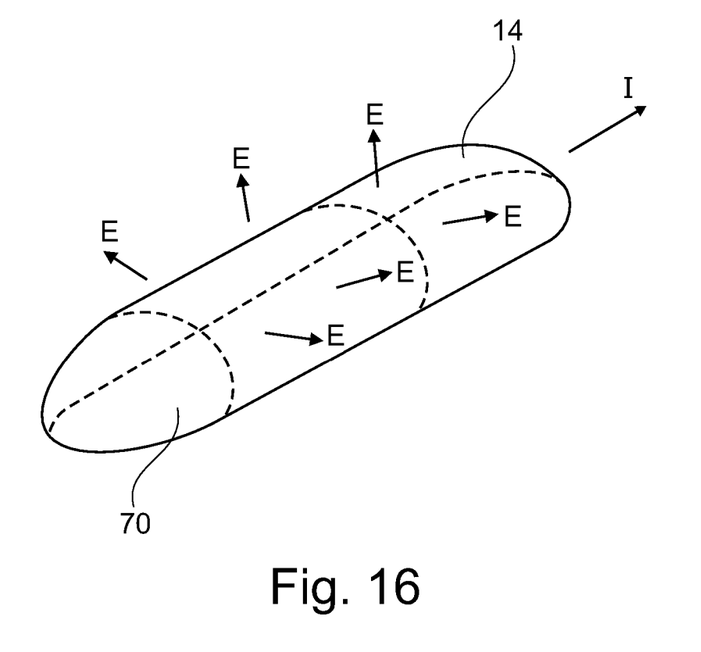
FIG. 16 illustrates an alternative in the shape of the expander.

FIGS. 15 and 16 illustrate alternative shapes of expander according to one or other or both of the above-discussed arrangements. FIG. 15 provides a semi-circular arrangement with a base 70 and a semi-circular domed top coating 14 or envelope 14e whilst FIG. 16 provides an elongate or semi-tubular arrangement having a similar base 70 and a curved but elongate top coating 14 or envelope 14e. The arrangement of FIG. 15 may provide a gentler edges to the profile of the implanted expander and, hence, less irritation for the patient whilst the arrangement of FIG. 16 may provide a slim-line option for easy insertion through smaller apertures or for insertion into areas where access is difficult.

The above-described manufacturing process provides an expandable implant 10 which may be used in medical and other procedures and which may be provided with both a delay before expansion and a controlled rate of expansion when initiated. Those skilled in the art will appreciate that the swelling pressure is provided by the hydration of the polymer network (e.g. xerogel) to form a fully swollen polymer network (e.g. a hydrogel) which occurs in vivo. The self-inflating polymer network is preferably a xerogel/hydrogel, i.e. the network changes from a xerogel to a hydrogel as it absorbs water in vivo. The self-inflating polymer network preferably generates a swelling stress pressure of up to 200 kPa1-50 kPa/cm2, and more preferably 2-20 kPa/cm2. The absolute swelling pressure may be up to 100 kPa and is preferably at least 30 kPa.

Those skilled in the art will appreciate that elements of the present invention may be used individually or in combination with each other.

The invention claimed is:

1. A tissue expander comprising:
a self-inflating core having a non-inflated state and an inflated state and a coating surrounding said core, in which said coating is applied directly to said core and includes a plurality of first and/or second apertures through said coating, and
wherein said coating and said core are separable from each other characterized in that said core includes an outer surface and said coating includes an inner surface where said coating is non-adhered to said core having no physical inter-bond between the inner surface of said coating and the outer surface of the core.

2. The tissue expander of claim 1, characterized in that said coating comprises a fluid impermeable material.

3. The tissue expander of claim 1, further including an inter-coating between the inner surface of the coating and the outer surface of the core.

4. The tissue expander of claim 1, characterized in that said coating comprises a molded coating molded around the outer surface of said core.

5. The tissue expander of claim 1, wherein said core has a top portion, a bottom portion, and a side portion,
wherein said coating surrounds said core and is in physical contact with at least a portion of the side portion of the core when said inner core is in said non-inflated state and out of contact with said side portion of the core when said inner core is in a partially inflated state.

6. The tissue expander of claim 5, wherein said core includes a first edge defined by said top portion and said side portion, wherein said coating has a greater thickness (T) adjacent said first edges than a thickness (t) along at least one of the top portion and the side portion of the coating,
wherein the first edge of the core has a radius of curvature (R) and said coating has a second edge adjacent said first edge having a radius of curvature (r),
wherein said radius (r) of said coating is less than said radius of curvature (R) of said core.

7. The tissue expander of claim 1, wherein said coating includes a top portion, a bottom portion, and a side portion where one or more circumferentially extending ring portions extend from said side portion of the coating.

8. The tissue expander of claim 7, wherein said core includes a top portion, a bottom portion, and a side portion and a first edge defined by said top portion and said side portion, the first edge having a radius of curvature (R)
wherein said coating has radius of curvature (r) adjacent said radius of curvature (R) of said core,
wherein said radius (r) of said coating is less than said radius of curvature (R) of said core.

9. The tissue expander of claim 1, characterized in that said coating comprises an envelope having an internal volume ($V^1$) and wherein an inner core comprises a plurality of separate expandable elements having a total (de-hydrated) volume ($V^2$) when inserted into said envelope and wherein volume $V^2$ is less than volume $V^1$.

10. The tissue expander of claim 9, characterized in that a hydrated volume of said plurality of separate expandable elements is substantially equal to or greater than the internal volume ($V^1$) of the envelope.

11. The tissue expander of claim 1, characterized by including a non-expandable base portion forming or integral with a portion of the coating.

12. The tissue expander of claim 1, characterized by including a semi-permeable barrier material within one or more of said first apertures for controlling the rate of water ingress.

13. The tissue expander of claim 1, characterized in that said core comprises a hydrophilic self-inflating polymer.

14. A method of manufacturing the tissue expander of claim 1, characterized by the steps of:
a. selecting a self-inflating hydrophilic core material;
b. forming said selected material to a given height H and width W;
c. compacting said core material by reducing the height H thereof whilst increasing the width W thereof such as to produce a compacted core;
d. applying a separable resilient fluid impermeable coating directly to said core; and
e. providing a plurality of first and/or second apertures through said coating.

15. The method of claim 14, characterized by the additional steps of:
f. partially hydrating said self-inflating hydrophilic core material between steps (a) and (b); and
g. de-hydrating said self-inflating hydrophilic core material between steps (b) and (c).

16. The method of claim 14, characterized by including the further steps of providing a semi-permeable material within one or more of said one or more first and/or second apertures,
wherein applying a coating directly to said core in step (d) is by molding said coating around said core.

17. A method of manufacturing the tissue expander of claim 1, characterized by the steps of:
a. selecting a self-inflating hydrophilic core material;
b. forming said selected material into a plurality of separate expandable elements;
c. injection molding an envelope having an internal volume ($V^1$) around said expandable elements;
d. providing a plurality of first and/or second apertures through said envelope.

18. The method of claim 17, characterized by the additional steps of:
a. partially hydrating said self-inflating hydrophilic core material between steps (a) and (b); and
b. de-hydrating said hydrophilic core material between steps (b) and (c).

19. The method of claim 17, characterized by including the step of inserting a semi-permeable material into said one or more apertures.

20. The method of claim 17, characterized by including the step of compacting said plurality of expandable elements between steps (b) and (c).

* * * * *